(12) United States Patent
Beale et al.

(10) Patent No.: US 10,325,070 B2
(45) Date of Patent: Jun. 18, 2019

(54) TREATMENT INTELLIGENCE AND INTERACTIVE PRESENCE PORTAL FOR TELEHEALTH

(71) Applicants: Ryan Gordon Beale, Huntington Woods, MI (US); Mark Ellis Jaruzel, II, Farmington Hills, MI (US)

(72) Inventors: Ryan Gordon Beale, Huntington Woods, MI (US); Mark Ellis Jaruzel, II, Farmington Hills, MI (US)

(73) Assignee: The Live Network Inc, Northville, MI (US)

( * ) Notice: Subject to any disclaimer, the term of this patent is extended or adjusted under 35 U.S.C. 154(b) by 0 days.

(21) Appl. No.: 15/377,490

(22) Filed: Dec. 13, 2016

(65) Prior Publication Data
US 2017/0169177 A1    Jun. 15, 2017

Related U.S. Application Data

(60) Provisional application No. 62/266,949, filed on Dec. 14, 2015.

(51) Int. Cl.
*G06F 19/00* (2018.01)
*G06N 20/00* (2019.01)

(52) U.S. Cl.
CPC ........ *G06F 19/3418* (2013.01); *G06F 19/321* (2013.01); *G06N 20/00* (2019.01)

(58) Field of Classification Search
CPC ........ G06Q 40/06; G06Q 50/22; G06Q 50/24; G06F 19/3418; G06F 19/321; G06N 20/00

USPC .......................................................... 705/2, 3
See application file for complete search history.

(56) References Cited

U.S. PATENT DOCUMENTS

| | | | | |
|---|---|---|---|---|
| 2005/0038669 | A1* | 2/2005 | Sachdeva | G06F 19/3481 705/2 |
| 2008/0249806 | A1* | 10/2008 | Dlugos | A61B 5/02055 705/3 |
| 2011/0118555 | A1* | 5/2011 | Dhumne | A61B 5/16 600/300 |
| 2012/0041911 | A1* | 2/2012 | Pestian | G06N 20/00 706/12 |
| 2014/0019149 | A1* | 1/2014 | Yu | G06F 19/3425 705/2 |
| 2014/0058189 | A1* | 2/2014 | Stubbeman | A61N 2/002 600/13 |
| 2014/0200913 | A1* | 7/2014 | Budhrani | G06Q 10/10 705/2 |
| 2014/0365234 | A1* | 12/2014 | Saunders | G06F 19/3418 705/2 |
| 2015/0012467 | A1* | 1/2015 | Greystoke | G06N 20/00 706/12 |

(Continued)

*Primary Examiner* — Igor N Borissov
(74) *Attorney, Agent, or Firm* — Kohn and Associates, PLLC (57) ABSTRACT

The present invention relates to a computerized system for and method of providing precision healthcare services such as consultation, education, assessment, diagnosis, intervention, or treatment at a distance via encrypted real-time image and audio presence where the healthcare professional's assessment, diagnosis, and intervention activities are informed by patient feedback, smart objects, and artificial intelligence and patient outcomes are optimized through recursive system feedback. The present invention is unlimited with regard to the type of patient entity or healthcare professional entity.

16 Claims, 6 Drawing Sheets

(56) References Cited

U.S. PATENT DOCUMENTS

2015/0261934 A1\* 9/2015 Miller ................ G06F 19/3456
705/3
2016/0378928 A1\* 12/2016 Benton ................ G06F 19/30
705/2

\* cited by examiner

TREATMENT INTELLIGENCE AND INTERACTIVE PRESENCE PORTAL FOR TELEHEALTH

REFERENCE TO RELATED APPLICATIONS

This application claims an invention which was disclosed in Provisional Application No. 62/266,949, filed Dec. 14, 2015, entitled "DYNAMIC AND INTERACTIVE VIEWING PORTAL FOR TELEMEDICINE, TELEHEALTH AND TELEPSYCHOLOGY". The benefit under 35 USC § 119(e) of the United States provisional application is hereby claimed, and the aforementioned application is hereby incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Field of the Invention

The invention pertains to the field of healthcare services. More particularly, the invention pertains to a computerized system for and method of providing precision healthcare services related to the AI-optimized assessment, diagnosis, and treatment of mental and emotional health and distress at a distance.

Description of Related Art

A mental health disorder, also commonly referred to as a mental illness, is a pattern of mood, cognition, behavior, or personality that occurs in a person and is thought to cause distress or disability that is not a normal part of development or culture. Mental health disorders are quite common. In the United States, the American Psychiatric Association estimates that over 68 million Americans will meet diagnostic criteria for a psychiatric or substance use disorder in a given year. The costs associated with treated, undertreated, and untreated mental illnesses are high with The World Economic Forum estimating worldwide costs were $2.5 trillion for 2010.

Access to adequate assessment and care for mental health disorders is lacking in many parts of the United States. The Substance Abuse and Mental Health Services Administration (SAMHSA) estimates that fewer than 50% of adults meeting diagnostic criteria for a mental health disorder receive any treatment for that disorder. There are also an estimated 90 million Americans presently living in identified Mental Health Provider Shortage Areas according the United States Department of Health and Human Services. The combination of stigma, low provider density areas, and inadequate treatment resources presently complicates the practice of mental healthcare.

One commonly employed treatment for mental health disorders is psychotherapy. Psychotherapy has been shown to be effective for treating many different specific diagnoses as well as for treating patients suffering from multiple comorbid diagnoses. Existing studies strongly suggest that psychotherapy is generally effective with an effect size greater than that of antidepressant medications. The literature suggests that the general effect size for psychotherapy is moderate to large (Cohen's d>0.5). There is currently debate in the literature about which specific interventions might be most advantageous for which specific disorders or which specific interventions might be most advantageous for which specific types of clients.

Recent advances in artificial intelligence (AI) and machine learning have rapidly accelerated the pace at which computer systems can match or surpass basic human expertise in tasks as diverse as playing chess, recommending products, answering trivia questions, suggesting cancer treatments, and driving cars. Applying these advanced AI systems to preliminary patient matching with treatment modality and subsequent treatment plan optimization, can improve outcomes in mental health treatment.

SUMMARY OF THE INVENTION

The present invention advantageously provides systems and methods to securely provide precision psychotherapy and other professional mental health interventions that are customized to the patient served at a distance. When patients initially interact with the system, they will bring with them a wealth of data derived from numerous sources. This data includes information such as demographic, genetic, assessment, diagnosis, treatment, history, outcome, wearable, mobile device, augmented reality device, social network, and totem data. When this data is vectorized, normalized, and coupled with patient input symptom description and healthcare professional input assessment and diagnostic information that has also been vectorized and normalized and the resulting vectors analyzed by AI methods, the system can suggest in-session interventions and prescribed homework assignments tailored to optimize patient satisfaction and outcome. The present invention is advantageous in that it allows healthcare professionals to more rapidly gain a picture of the patient's actual behaviors, something patients seeking mental health services may be less willing or able to accurately report on in the initial stages of treatment.

The system is continually learning in a recursive manner such that the output of one set of patient experiences are used to train the AI system to further refine future patient recommendations with regard to such treatment variables as individual healthcare professional, professional theoretical orientation, professional efficacy rating, professional discipline, professional technical expertise, professional demographic data, in-session interventions, prescribed homework assignments, frequency of contact, potential need for additional services, and prognosis at the termination of services.

The system will allow one or more patients and one or more healthcare professionals to connect with each other so that they can securely meet via encrypted, mutual, real-time image and audio presence. This system will allow professionals to provide professional consultation, education, assessment, diagnosis, intervention, or treatment at a distance. The system will support the healthcare professional's decision process with real-time data displays about the patient's mood derived from real-time analysis of the patient's speech (tone analysis) and facial expressions (microexpressions) during session as well as a display of pertinent AI-informed data from the patient's history. The system will also display feedback about the patient's present circumstances and adherence to prescribed homework regimes.

The system will continually monitor patient follow up with prescribed homework activities via a system of patient reminders and prompts. Depending on the devices available to the patient and permissions given by the patient, the system will be able to send reminders to the patient about prescribed homework activities. The patient will be able to mark the given activity as completed, incomplete, or choose to snooze the activity such that the system will prompt them again later. Each such action on the part of the client will be logged by the system and included as a part of the patient's treatment record and also logged and vectorized and normalized to allow for AI training and optimization, allowing both the healthcare professional and patient a much more accurate view of in-vivo adherence to recommended interventions and allowing the system to improve treatment recommendations and outcomes.

The overall system will give patients better chances for positive experiences and positive outcomes. The system will assist in finding the best fit between patient and healthcare professional variables. The system will help the healthcare professional and client make more honest and accurate determinations about the effectiveness of interventions during the course of the treatment rather than only after the fact (if at all). In short, the system will assist the healthcare professional and patient by generating predictive and prescriptive analytics rather than merely (post hoc) descriptive analytics. The system will assist the users in transcending the distances between patient need and effective professional assistance.

The present invention is not intended to be limiting in the nature of the entity that is the healthcare provider nor the nature of the entity that is the patient. It is expected that the present invention will be used by a diverse range of healthcare professionals and patients.

BRIEF DESCRIPTION OF THE DRAWINGS

Further advantageous features of the present invention will become more apparent when the following detailed description is taken along with reference to the accompanying drawings in which.

DETAILED DESCRIPTION OF THE INVENTION

As discussed above, the present invention relates to a computerized system for and method of providing precision healthcare services related to the AI-optimized assessment, diagnosis, and treatment of mental and emotional health and distress at a distance. Several aspects of the present invention provide novel advances in the provision of telemedicine and telepsychology (sometimes also referred to as: "telehealth," "telemental health," "telepsychiatry," and "telebehavioral health") and the system as a whole provides a novel integrated platform for the provision of healthcare interventions, especially psychotherapeutic interventions, at a distance. The present invention combines clinical processes, communications software, and vectorized AI processes into a novel platform that offers clinical insights and improved outcomes that would not be possible with any of the components alone and thus represents an improvement upon the art of psychotherapy and makes possible precision psychotherapy.

Embodiments of the present invention will accelerate the interactive dialogue between healthcare practice, interventions, and outcomes. The present system allows for iteration and recursive learning to occur in real time or near real time so that patients and healthcare professionals can make treatment decisions informed by outcome information during, rather than after, the course of treatment. The system as a whole could eventually be informed by many thousands of years of professional experience and many thousands of lived years of patient experience. Using the wisdom and information about distress and the amelioration of distress that is both explicitly and tacitly contained within these users, the system will begin to recognize previously unknown patterns in real time so as to suggest additional treatment options for consideration. This will allow for unprecedented treatment matching both at the level of general interventions for general disorders and at the level of the individual patient and their unique presentation.

Figure 1:
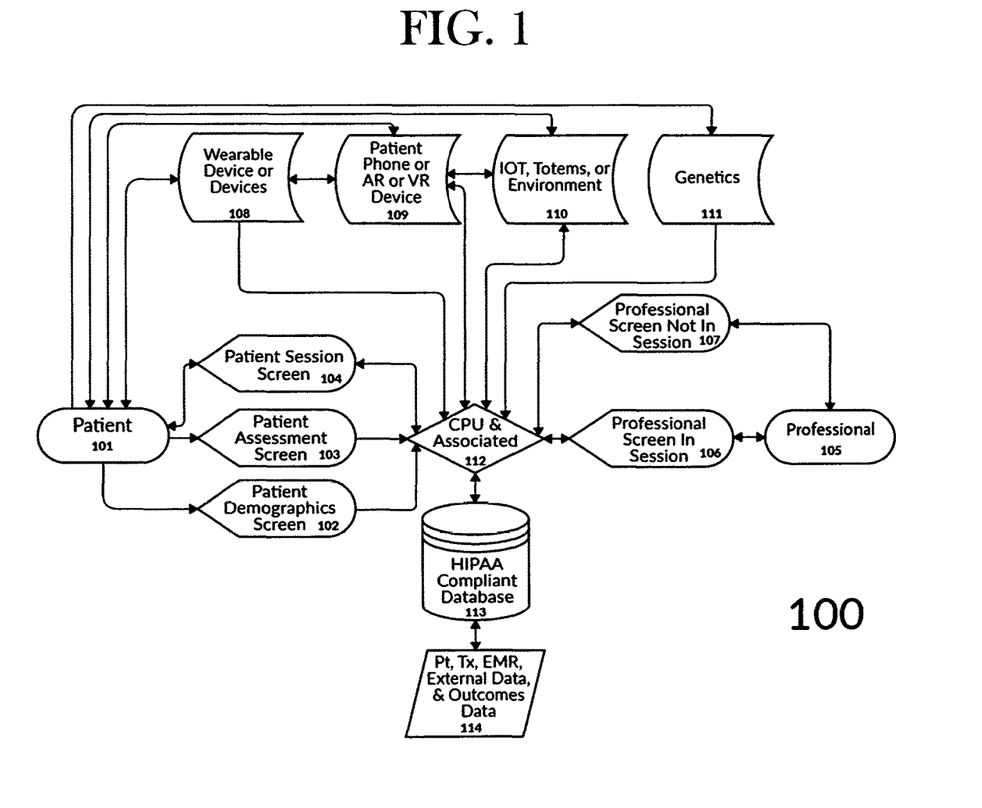
FIG. 1 shows a functional block diagram of hardware, software, or a combinational instance thereof that may be implemented in one or more computer systems or processing systems, whether local or cloud based, to carry out the functionality of the system as a whole, in accordance with one embodiment of the present invention.

FIG. 1 illustrates a functional block diagram of an example computing system 100 in accordance with one embodiment of the present invention. The example computing system 100 shows how a patient 101 can receive professional services from a healthcare professional 105 at a distance that are informed by patient data derived from a diversity of sources. The example computer system could be comprised of hardware, software, or a combinational instance thereof that may be implemented in one or more computer systems or processing systems, whether local or cloud based, to carry out the functionality of the system as a whole.

In this system 100, a patient 101 will contribute data to the system through a range of means. The patient 101 will directly enter relevant demographic information about themselves through a patient demographics screen 102. The patient 101 will also answer questions designed to elicit aspects of their personality, strengths, weaknesses, and present symptomology through one or more assessment instruments presented to them through the patient assessment screen 103. The patient 101 will also give permissions to a range of external devices or third-party databases of information via existing APIs or APIs to be developed specifically for this purpose. These permissions could include data from wearable devices 108, data from the patient's smartphone or augmented reality interface device 109, data from objects that are a part of a smart environment or the internet of things 110, and the patient's genome or genetic profile 111.

In this system 100, the patient demographics screen 102 serves as a graphic interface for the patient 101 to enter relevant demographic information including (but not limited to): legal name, nickname, date of birth, sex, gender, race, ethnicity, marital status, educational attainment, parent educational attainment, socioeconomic status, veteran status, parental status, religion or religious preferences, known drug allergies, and emergency contact person. The information from the patient demographics screen 102 is transmitted to the processor 112 and stored in a HIPAA-compliant database 113 in one embodiment of this system 100.

In this system 100, the patient assessment screen 103 serves as a graphic interface for the patient 101 to take assessments or enter data designed to offer a portrait of relevant aspects of their personality, strengths, weaknesses, past symptomology, present symptomology, and current level of risk. This interface 103 may present a single, comprehensive, assessment instrument or several different assessment instruments to the patient. In one embodiment of this system, the patient will be presented with a series of questions that are followed by movable sliders for the patient to indicate their relative score on a given item. The information from the patient assessment screen 103 is transmitted to the processor 112 vectorized, and stored in a HIPAA-compliant database 113 in one embodiment of this system 100. Additional information about this particular screen is given in FIG. 2.

Once a patient 101 has completed sufficient information with the system 100, they will be able to meet with a healthcare professional 105. This is accomplished by means of a patient session screen 104. The physical screen this session screen 104 appears on could be one of a range of interfaces including (but not limited to): a computer screen, a smartphone screen, a tablet screen, or an augmented reality screen or similar interface where a physical screen is lacking. While interacting with the patient session screen 104, the patient will have encrypted real-time access to the image and audio presence of a healthcare professional 105 available for consultation, education, assessment, diagnosis, intervention, or treatment. The patient session screen 104 will also log any data from in-session patient 101 behavior such as emotional content as evidenced by tone or microexpressions to the processor 112 where it will be vectorized and stored in the HIPAA-compliant database 113. Additional information about this particular screen is given in FIG. 3.

In this system 100, a healthcare professional 105 will contribute data to the system through a range of means. Through both the in-session screen 106 and the not-in-session screen 107, the professional 105 will be able to select and identify in-session interventions as well as homework assignments. The professional 105 will also enter assessments, diagnoses, and prognoses into the system. They will also be able to meet with a patient 101 via encrypted real-time image and audio presence to provide professional consultation, education, assessment, diagnosis, intervention, or treatment. The professional 105 will also receive feedback about the patient's adherence to prescribed treatments, receive suggestions about optimized treatment interventions derived from AI-output predictions informed by training on a range of vectorized and normalized data, and receive additional data about the patient's psychological state and recent behaviors derived from AI-output assessments, patient report, standard clinical instruments taken, and emotional state as suggested by vocal tone and microexpressions.

The professional 105 will primarily interact with the patient 101 through the professional in-session screen 106 where the professional will be presented with an encrypted real-time image and audio presence of the patient 101. The professional 105 will also receive real-time data about the patient's mood via tone analysis and microexpression analysis. Via this screen 106, one or more professionals 105 will be able to provide professional consultation, education, assessment, diagnosis, intervention, or treatment to one or more patients 101. This display 106 will also show the professional a summary of key portions of the patient's recent treatment history. This screen will have output data sent to it from the processor 112 and the HIPAA-compliant database 113. It will also log any changes made by the professional 105 to the processor 112 and the HIPAA-compliant database 113. Additional information about this particular screen is given in FIG. 4.

The professional 105 will also interact with the not-in-session screen 107. Through this screen 107, the professional 105 will be able to verify content of the sessions conducted over the in-session screen 106 including session time, in-session interventions, and changes to homework assignments. This screen 107 will populate with information drawn from the HIPAA-compliant database 113 and will be an up-to-date summary of the treatment for the patient 101. Additional information about this particular screen is given in FIG. 5.

One of the distinguishing features of this system 100 will be the ways in which it draws on external data from devices in the life of the patient 101. The system 100 will take in data from wearable devices 108 that the patient 101 carries with them throughout their day. These devices 108 will convey a range of health and activity data about the patient 101 that will serve to augment the total picture of their emotional and behavioral health. This data will be vectorized and stored in the HIPAA-compliant database 113. This vectorized data will be normalized and serve as the raw material for the CPU and associated systems 112 to analyze using AI methods for emerging trends in the patient's treatment. Data from these devices, once vectorized and combined with vectorized data about other aspects of the patient's life and treatment, will support deeper insights into the patient's level of function, prognosis, and ideal psychotherapeutic interventions.

The smartphone, augmented reality device, or other primary interface device 109 will serve as an important node within the system 100. Depending on the devices available to the patient 101 and the permissions that they have given, this device 109 could serve to offer data about their behavioral and emotional state, serve as a display for the patient session screen 104, serve as a prompt to follow-up with assigned homework activities, or serve as an important node with connections to wearable devices 108 or the internet of things 110. The device 109 will likely communicate with several aspects of the system and serve as the primary interface for many patients 101. This system 100 could make use of such devices 109 via a range of different embodiments including both existing APIs and novel, downloadable, applications.

Environments are increasingly becoming smart environments where consumer products and devices are increasingly capable of transmitting information about their state, the state of the environment around them, and the state of their owners. The present system 100 will draw from a range of devices related to the internet of things 110 in order to augment the holistic picture of the patient 101 served. These devices 110 may communicate directly to the CPU and associated subsystems 112 or indirectly via relay through a smartphone or similar device 109. The data so derived, will be vectorized and will allow the AI aspects of the system 100 to detect emerging trends before humans might be aware of them.

This system 100 will also take input from the patient 101 in the form of accessing existing genetic profiles or the patient's entire genome if available 111. This data may serve to better optimize the system 100 to the unique needs of each patient 101.

This system 100 relies on a CPU and associated subsystems 112 to perform computation, execution of functions, and the reading and writing of information to the HIPAA-compliant database 113. This could be implemented in any number of ways with variations in software and hardware configurations (including CPUs, GPUs, TPUs, etc). In one embodiment of this system 100, the CPU and associated subsystems 112 are remotely based and implemented via servers and connections across the internet. In this embodiment, it is primarily a combination of software and cloud storage that facilitate the functioning of the system 100, with other portions feeding in information from external devices or databases (108, 109, 110, 111) and the CPU 112 receiving this information and writing it to the HIPAA-compliant database 113 (often in a vectorized and normalized form that is amenable to AI training) and sending out commands or information as appropriate (104, 106, 107, 109, 110). Additional detail about the ways in which the CPU and associated subsystems 112, the HIPAA-compliant database 113, and the content of the database 114 function together to make the system an artificially intelligent tool for treatment optimization can be found FIG. 6.

Figure 2:
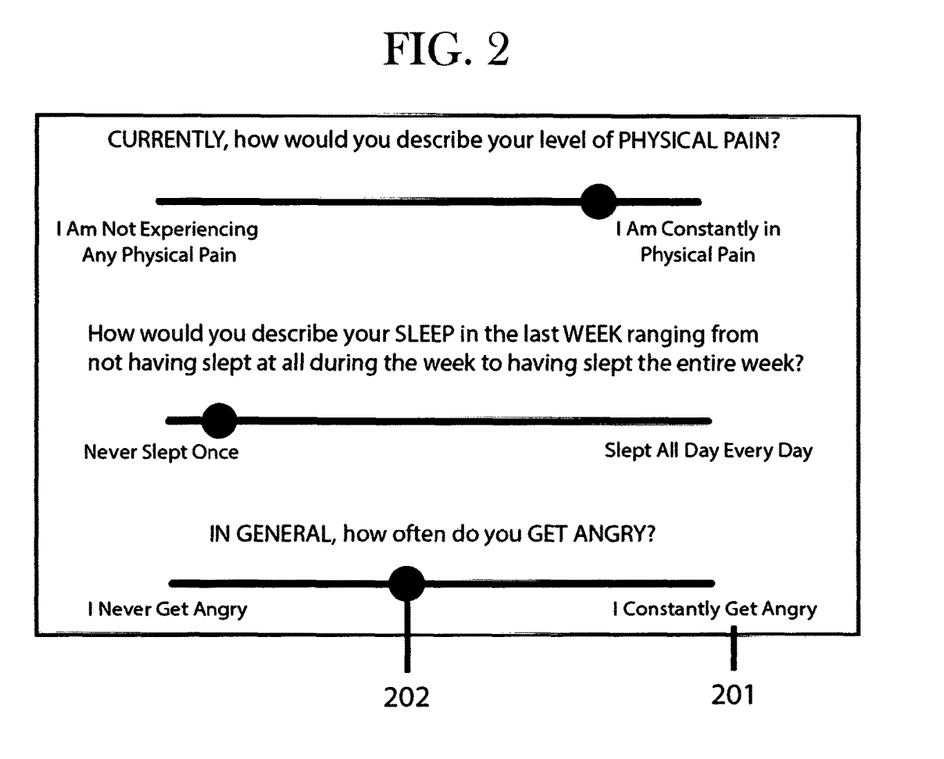
FIG. 2 shows an example of the patient assessment screen graphical user interface according to one embodiment of the present invention.

FIG. 2 illustrates one example of the patient assessment screen 103 previously described in FIG. 1. In this example, the person interacting with the graphical interface will be presented with dichotomous statements or polarities 201 about general personality, health habits, and present symptomology. They will move the indicator 202 in the middle of the line to the place on the line that they believe best represents what is true for them. These sliding assessments will generate a larger, granular, range of numerical values that can contribute to the system's overall understanding of the patient and allow the system to make novel predictions about the patient's health status, diagnosis, optimal psychotherapy interventions, and prognosis.

Figure 3:
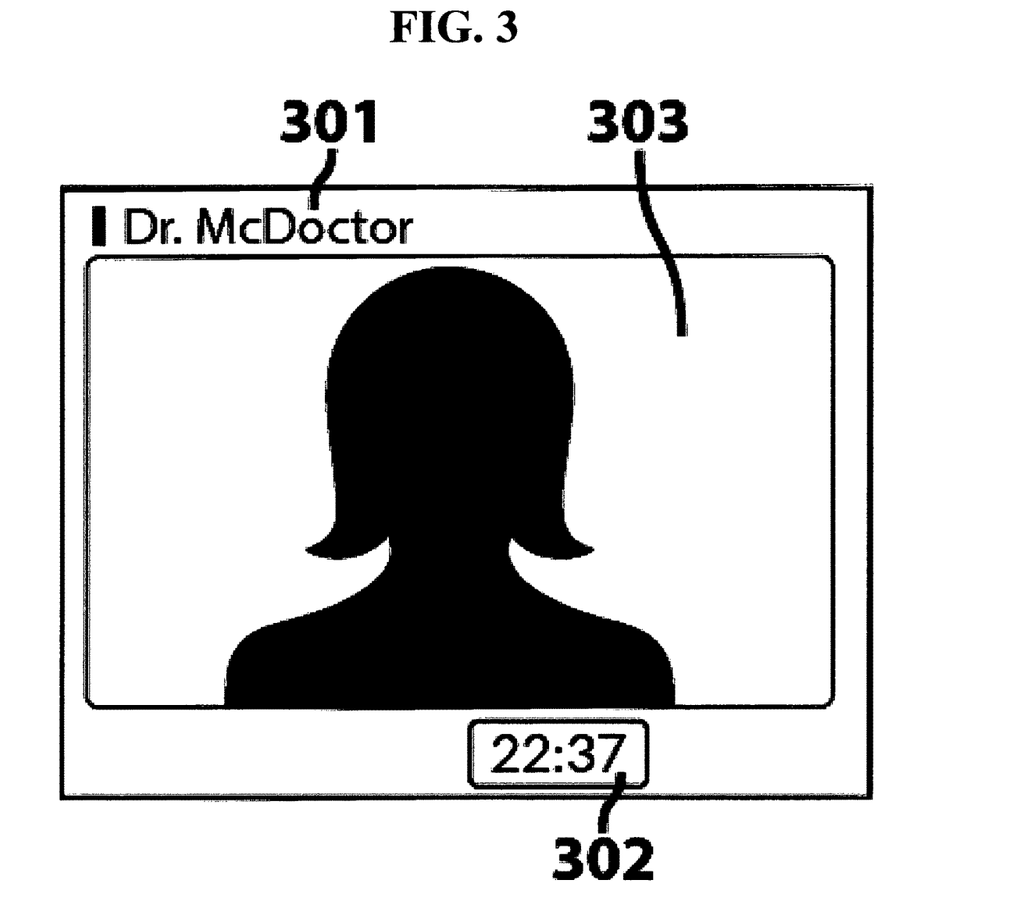
FIG. 3 shows an example of the patient in-session encrypted real-time image and audio presence view according to one embodiment of the present invention.

FIG. 3 illustrates one example of the patient in-session screen 104 previously described in FIG. 1. In one embodiment of the present invention, this screen features the name of the healthcare professional providing services 301. This screen also features a clock 302 indicating how long the current session has been underway. Most importantly, this screen displays the encrypted, real-time, audio and video presence of a healthcare professional 303 so that interactive professional services can be received at a distance.

Figure 4:
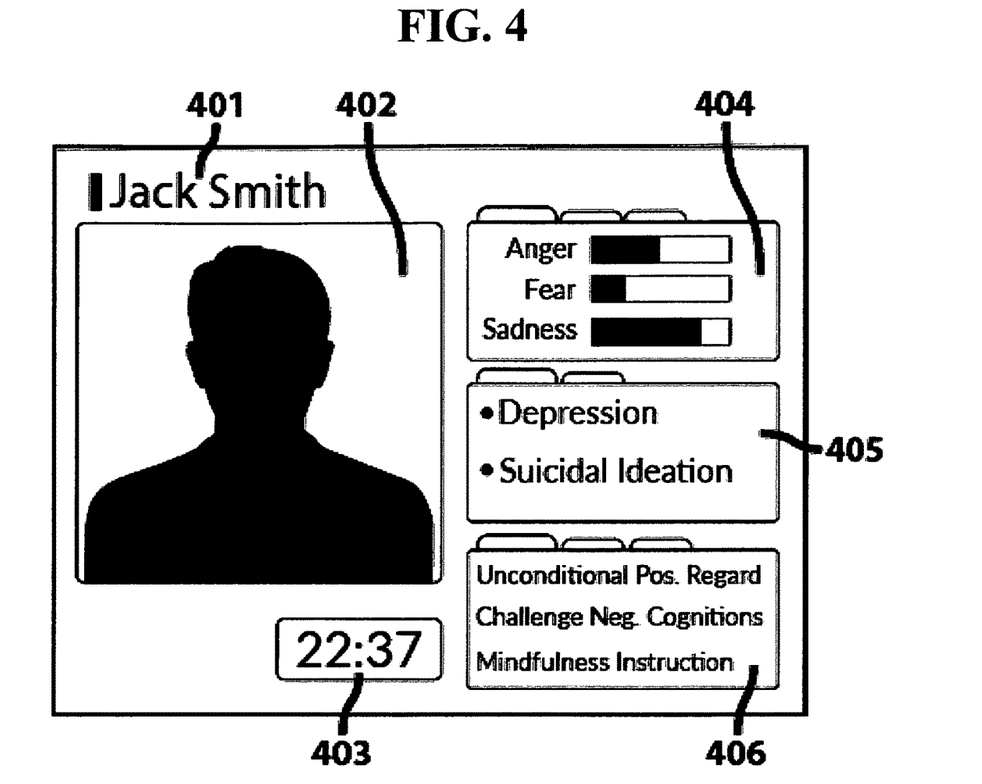
FIG. 4 shows an example of the healthcare professional in-session encrypted real-time image and audio presence view with accompanying client data drawn from real-time interaction as well as previously available data according to one embodiment of the present invention.

FIG. 4 illustrates the professional in-session screen 106 previously introduced in FIG. 1 in much greater detail. In one embodiment of the present invention, the name of the patient being seen is prominently displayed 401. The patient's encrypted, real-time, audio and visual presence is also displayed 402 facilitating the interactive offering of professional services. This screen also features a clock 403 indicating how long the current session has been underway. The screen displays real-time feedback from mere systems designed to offer insight into the patient's current emotional state via AI analysis of vocal tone and facial microexpressions 404. The display shows aspects of the patient's history that may be relevant to the current session such as past and present diagnoses and current areas of focus 405. In one embodiment of the present invention, the professional will be able to switch between tabs and review other aspects of the patient's file while in session with that patient 406.

Figure 5:
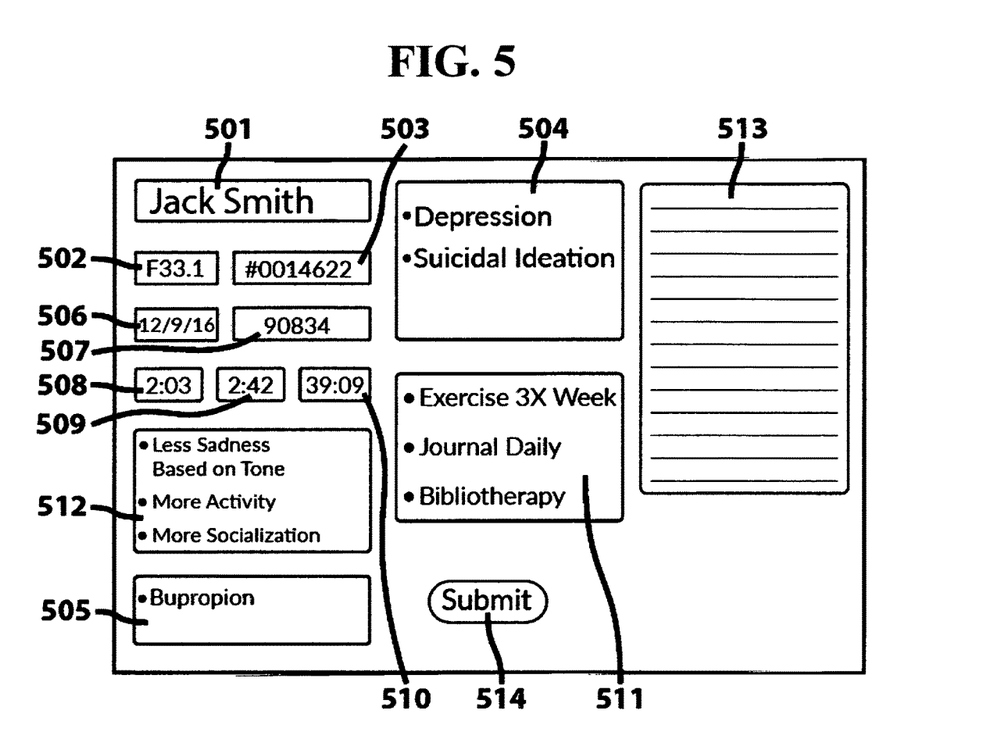
FIG. 5 shows an example of the healthcare professional not-in-session encrypted portal for reviewing patient assessments, diagnoses, treatment, and progress to date as well as other aspects of the patient's record according to one embodiment of the present invention.

FIG. 5 illustrates the professional not-in-session screen 107 previously introduced in FIG. 1 in much greater detail. In one embodiment of the present invention, the name of the patient appears on this screen 501. In one embodiment of the present invention the screen informs the professional of important information about the patient's case including: diagnosis 502, patient identification number 503, patient history 504, and any medication currently prescribed 505. These fields can be edited and updated by the professional. The screen also summarizes important information about the last session with the patient including: date 506, service or procedure provided 507, start time 508, stop time 509, duration 510, currently prescribed homework 511, changes in treatment 512, and any additional notations that the professional might wish to make 513. In one embodiment of the present invention, the professional can press a submission button to make the session note a permanent part of the patient's record 514. Most of the aforementioned fields are auto-populating fields that are filled in with data the system has previously recorded. The professional can edit them, but it is likely that this feature will shorten the duration of time that the professional will need to spend on paperwork.

Figure 6:
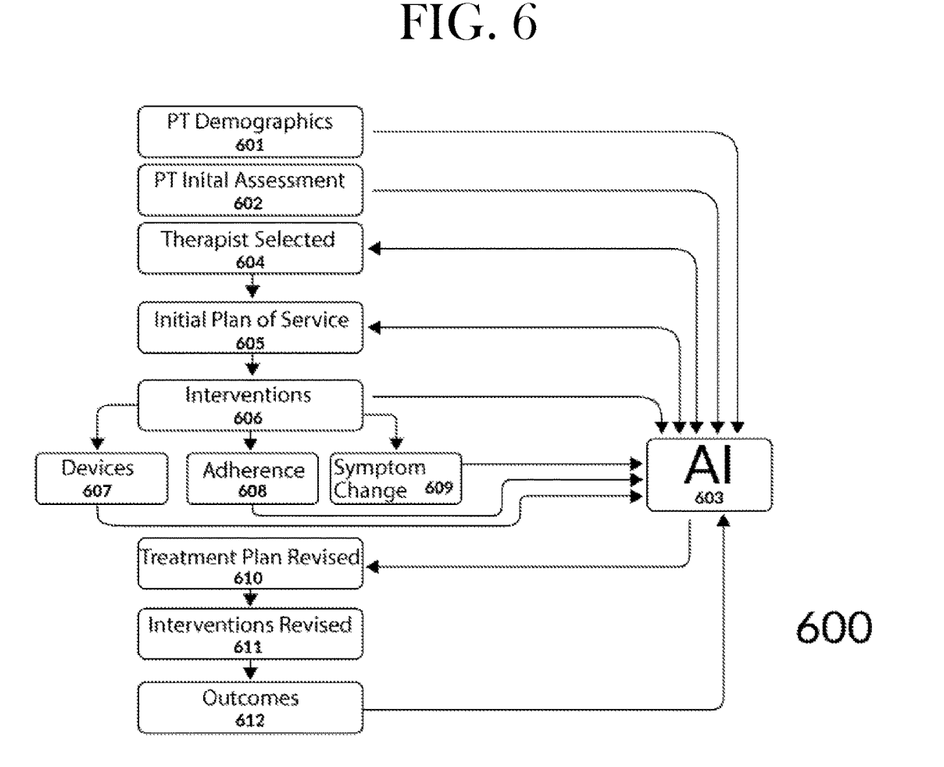
FIG. 6 shows how AI processes recursively use vectorized outcome data and other vectorized data to inform future patient and healthcare provider suggestions regarding treatment according to one embodiment of the present invention.

FIG. 6 describes the process flow for the artificial intelligence (AI) portion of the presently described invention 600. A large part of what makes the system as a whole 100 advantageous to professionals and patients alike, is the introduction of AI methods to optimize treatment selection and to provide recursive feedback to the system as a whole about the relationships between various professional variables, client variables, treatment variables, and outcomes.

The system starts with input from the patient in the form of patient demographics 601 and initial or formative assessments 602. The AI system 603 using methods such as (but not limited to): vectorization and skip thought vectors then suggests professionals based on a range of variables including but not limited to: interventions typically employed, prognoses, homework assignments given, theoretical orientation, efficacy rating, discipline, and professional demographic data. In one embodiment of the present invention, the system will present two clearly labeled lists indicating that one is a random selection of professionals in the patient's geographical vicinity and that the other is a selection of professionals in the patient's geographical vicinity likely to be a good fit for persons such as the patient. This second list has been generated by the AI component of the system after analyzing the patient input in the form of patient demographics 601 (broadly considered to include basic demographics as well as patient profile with regard to available device information for which the patient has given access/permission) and patient initial assessment results 602. The AI component of the system takes the available patient information (transformed into a vectorized format)

and makes predictions about professionals that are likely to be a best fit (based on the AI system that is has been trained on similar vectorized information paired with outcomes labels about previous patients). It is likely that this second list will provide the patient with a better recommendation in terms of likelihood of positive outcome than other existing methods would, whether generated by human judgment or algorithmic sorting (i.e. random assignment, simple specialty matching, professional referral, simple satisfaction ratings, simple linear correlation, etc.).

Whether the patient acts on the AI recommendations for a professional or not, they will need to select professional in order to proceed 604. The patient's choice of professional is logged by the AI system 603 and it uses the combination of patient and professional variables to suggest optimal treatment options to the professional for inclusion within the initial plan of service 605. More specifically, the patient variables that have been collected via patient input or device input as described in FIG. 1 and that have been vectorized and normalized are used by the AI system to make predictions about the treatment interventions (both in-session and between-session interventions) that are likely to be the most advantageously employed in the psychotherapeutic relationship between the particular patient and the particular professional selected by the patient. The patient's choice of professional is logged by the system and the professional's characteristics and demographics are also logged by the system in a vectorized format for later training and updating of the AI system once an outcome or discharge label has been entered. Thus, the data so collected here serves both to assist the particular patient and professional in their psychotherapeutic engagement and to assist future patients and professionals through the recursive training of the AI system.

Unlike other treatment algorithms where all patients with a given diagnosis are offered a single treatment assumed to be best (often based on information from small-number clinical trials in contexts that differ from typical day-to-day professional practice or based on low-variance/high-bias statistical models), the AI system 603, informed by high volume and high dimensionality data, in one embodiment of the present system will offer the professional four distinct sets of "top 5" interventions for the patient's identified focus or diagnosis. It will offer a list of the professional's own 5 most commonly utilized interventions by simple frequency. It will offer a list of the 5 most commonly utilized interventions by the professional's particular profession (psychologist, social worker, nurse, psychiatrist, etc.). It will offer a list of the 5 most commonly utilized interventions by the professional's theoretical orientation (cognitive, behavioral, psychodynamic, humanistic, family systems, etc.). It will also offer a suggested list of optimized interventions based on the total available data within the AI-informed system. This is where the system advantageously differentiates itself from other typical practices or existing systems. The optimized interventions that the AI system will offer are based on vectorized data drawn from myriad dimensions of the patient's life including: self-report data (demographics, assessment answers, etc.), objective device-report data (distance walked, activity, etc.), social network behaviors (including likes, activity, etc.), and professional assessment (diagnosis, prognosis, etc.). Given the wide range of types of data and categories of sources of data contribution, the present system will be able to make suggestions that go well beyond even expect clinical intuition. The professional will be free to use or not use any of the given recommendations as the system, in one embodiment of the present invention, will defer to the professional's judgment. In any case, the professional will create an initial plan of service 605 and the composition of this plan will be recorded by the AI system 603 in a vectorized format for later training and updating of the AI system once an outcome or discharge label has been entered. Thus, the data so collected here serves both to assist the particular patient and professional in their psychotherapeutic engagement and to assist future patients and professionals through the recursive training of the AI system.

The initial plan of service 605 will contain a range of interventions 606 that may consist of some combination of in-session interventions and prescribed homework. Homework interventions will be coded as such in the initial plan of service 605 and the AI system 603 will send out queries or reminders around those interventions. For example, in one embodiment of the present invention, the professional may prescribe "exercise as tolerated 3 times per week" to the patient. The AI system 603 will send out notifications to one or more of the patient's devices 607 to remind the patient to do the activity and/or to inquire as to whether the patient has completed the activity. If the patient reports "yes," the system 603 will record this. If the patient reports "no," the system 603 will record this. If the patient "snoozes" the reminder and/or reports "not yet," the system 603 will prompt the patient again at a later time. This adherence data 608, taken as a whole, will be recorded and vectorized by the AI system 603 and used to make additional predictions and/or recommendations about the particular patient and their particular course of treatment as well as stored in a vectorized format for later training and updating of the AI system once an outcome or discharge label has been entered. Thus, the data so collected here serves both to assist the particular patient and professional in their psychotherapeutic engagement and to assist future patients and professionals through the recursive training of the AI system with regard to homework adherence and efficacy for particular kinds of patients with particular kinds of mental and emotional distress.

After some period of time, the AI system 603 will analyze feedback from patient devices 607, patient adherence to prescribed homework 608, and any changes in symptoms 609 and use this information to suggest advantageous revisions to the initial plan of service 605, in the form of a revised treatment plan 610. The AI system will do this by comparing one or more vectors comprised of vectorized patient data with predictions based on the AI system's learning from previous training on vectorized information from past patients using the system. The professional, in consultation with the patient, is free to accept or reject any of these proposed changes or to make other non-proposed changes. In any event, the next iteration of the treatment plan begins 610 and the new interventions 611 are pursued in much the same manner as the original ones. This process will likely have numerous iterations with each iteration contributing to additional learning of the AI system and benefiting from the additional learning that the AI system has done in the interim, but for the sake of brevity, only a single iteration will be described here.

At the end of treatment, the final outcomes 612 are vectorized, logged to the AI system 603, and stored as outcome labels that will be used to inform the system as a whole about how to further optimize for patient satisfaction and positive outcome. As the system grows in size, it will accumulate vectorized data generated by many clinicians of differing professional training, experience levels, and theoretical orientations and use this novel information to assist the professionals in offering their best possible services to the patients served. This system will represent a truly novel addition to the field of healthcare in general and psychotherapy in particular. It avoids a simplistic model of a single treatment for a single (assumed to be homogenous) diagnosis, in favor of a complex, high dimensionality, model offering the promise of delivering precision psychotherapy interventions to patients in need. These precision psychotherapy interventions will be based on a 360-degree view of the patient that includes their understanding of themselves, their patterns of interaction within their social networks, their behavioral patterns as recorded by objective devices, their condition as assessed by competent professional expertise, and the specific profile of each of these as analyzed by an AI system that takes in this high volume and high variety data and constructs a high dimensionality picture of the patient being served in order to suggest more accurate diagnostic formulations and more advantageous interventions than would likely be within the ability of either human clinicians or typical statistical frameworks employed in psychotherapy outcomes research.

Various user interfaces and embodiments were described above in some detail with reference to the drawings, wherein like reference numerals represented like parts and assemblies throughout the several views. Any of the preceding references to the various embodiments does not limit the scope of the claims attached hereto. Additionally, any examples set forth in this specification are not intended to be limiting and merely set forth some of the many possible embodiments for the appended claims. It is understood that various omissions and substitutions of equivalents are contemplated as circumstances may suggest or render expedient, but these are intended to cover applications or embodiments without departing from the spirit or scope of the claims attached hereto. Also, it is to be understood that any of the phraseology and terminology that were used herein were for the purpose of description and should not be regarded as limiting.

Any of the devices/servers/CPUs in the above-described systems may include a bus or other communication mechanism for communicating information, which interconnects subsystems and devices, such as processor, system memory (e.g., RAM), static storage device (e.g., ROM), disk drive (e.g., magnetic or optical), communication interface (e.g., modem or Ethernet card), display (e.g., CRT or LCD), input device (e.g., keyboard, touchscreen). The system component performs specific operations by the processor executing one or more sequences of one or more instructions contained in system memory. Such instructions may be read into system memory from another computer readable/usable medium, such as static storage device or disk drive. In alternative embodiments, hard-wired circuitry may be used in place of or in combination with software instructions to implement the invention. Thus, embodiments of the invention are not limited to any specific combination of hardware circuitry and/or software.

Any use of the word "screen" above should be taken to mean a range of interfaces including but not limited to: a computer screen, a smartphone screen, a tablet screen, or an augmented reality screen or similar interface where a physical screen is lacking. Any references to a screen anywhere above are for the sake of brevity and should not be construed as a limitation on the types of devices or interfaces that can be utilized in various embodiments of this invention.

In an embodiment of the invention, execution of the sequences of instructions to practice the invention is performed by a single computing system. According to other embodiments of the invention, two or more computing systems coupled by a communication link (e.g., LAN, PTSN, or wireless network) may perform the sequence of instructions required to practice the invention in coordination with one another. The system component may transmit and receive messages, data, and instructions, including program, i.e., application code, through communication link and communication interface. Received program code may be executed by the processor as it is received, and/or stored in disk drive, or other non-volatile storage for later execution.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Methods recited herein may be carried out in any order of the recited events which is logically possible, as well as in the recited order of events.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

Accordingly, it is to be understood that the embodiments of the invention herein described are merely illustrative of the application of the principles of the invention. The breadth of the present invention is not to be limited to the examples provided, illustrated embodiments and/or the subject specification, but rather only by the scope of claim language associated with this disclosure.

SEQUENCE LISTING

Not Applicable

What is claimed is:

1. An integrated computer-implemented system for providing secure telehealth and teletherapy services informed by artificial intelligence and patient feedback comprising:
   a physical database configured to store application data, patient data including demographic, genetic, assessment, diagnosis, treatment, history, outcome, wearable, mobile device, augmented reality device, and social network, and professional data including assessment, diagnosis, treatment, intervention, prognosis, homework assignment, theoretical orientation, efficacy rating, discipline, and demographic data both in a raw form and a vectorized form where each patient has one or more vectors comprised of the aggregation of numerous, diverse, data points about them;
   a physical or virtual display configured to display a patient's real-time image and audio presence and relevant emotional, clinical, behavioral habit, and feedback data to a healthcare professional and
   a computer-implemented physical processor or collection of processors configured to use artificial intelligence to analyze patterns in vectorized patient data, to transmit data to and receive data from patients across a range of devices and interfaces including smart phones, mobile devices, augmented reality displays, wearables, and smart devices, to transmit data to and receive data from a healthcare professional, and to receive and execute commands from one or more healthcare professionals, to continually learn from outputs of patient experiences that are added to said system that further refine further patient recommendations, wherein said computer-implemented system is configured to:
   receive patient information chosen from the group consisting of symptom data, demographic data, genetic data, diagnostic data, treatment data, history data, outcome data, wearable data, mobile device data, augmented reality device data, social network data, and combinations thereof;
   store the patient information in the database in a vectorized form;
   analyze the vectorized patient information via low-rank matrix factorization and suggest at least one healthcare professional to be used;
   receive a selection from the patient of a healthcare professional;
   suggest intervention processes to the healthcare professional for the patient based on the patient information, healthcare professional demographic and theoretical orientation data, and vectorized data from previous patients analyzed via low-rank matrix factorization;
   receive from the healthcare professional an initial plan of service for the patient, the initial plan is based on the suggested intervention processes;
   connect a patient's device to the healthcare professional to receive real-time image and audio on the computer-implemented system and to provide in-session therapeutic intervention process based on the initial plan of service;
   augment the healthcare professional's in-session therapeutic intervention process with real-time data displays about the patient's mood derived from real-time analysis of the patient's speech including tone analysis, and facial expressions including microexpressions, by providing said real-time data to the healthcare professional during the in-session therapeutic intervention process in which the healthcare professional providing the service for the patient over the computer-implemented system chosen from the group consisting of consultation, education, assessment, diagnosis, intervention, treatment, and combinations thereof;
   analyze feedback from the patient in real-time and suggest revisions to the initial plan of service during the in-session therapeutic intervention process, and
   push clinical homework activities assigned by the healthcare professional during the in-session therapeutic intervention process to at least one patient device.

2. The system of claim 1, wherein the patient is a person or other entity seeking professional consultation, education, assessment, diagnosis, intervention, or treatment related to psychotherapy or psychoeducation.

3. The system of claim 1, wherein the healthcare professional is a person or other entity seeking to offer professional consultation, education, assessment, diagnosis, intervention, or treatment related to psychotherapy, psychoeducation, or similar professional activities.

4. The system of claim 1, wherein the database has been secured through encryption.

5. The system of claim 1, wherein the transmission of the patient's real-time image and audio presence and relevant data has been secured through encryption.

6. The system of claim 1, wherein the transmission of the healthcare professional's real-time image and audio presence and relevant data has been secured through encryption.

7. The system of claim 1, wherein the computer-implemented processor has been configured to use artificial intelligence including low-rank matrix factorization, vectorization and skip thought vectors to analyze patterns in vectorized patient assessments, genetics, diagnoses, treatments, outcomes, wearables, mobile devices, augmented reality devices, and social networks suggest prognosis and clinical interventions for an individual patient including in-session interventions, patient homework, prescribed activities, and therapeutic orientation.

8. The system of claim 1, wherein the computer-implemented processor has been configured to transmit homework treatment recommendations to patients across a range of devices and interfaces including smart phones, mobile devices, augmented reality displays, wearables, and smart devices and receive feedback about patient adherence to the treatment recommendations across a range of devices and interfaces.

9. The system of claim 1, wherein the computer-implemented processor has been configured to transmit predictive data derived from artificial intelligence processes informed by vectorized patient data and treatment adherence data about a patient to a healthcare professional to support professional psychotherapeutic activities.

10. The system of claim 1, wherein the computer-implemented processor has been configured to receive raw and predictive data about patient treatment adherence from a range of devices including smart phones, mobile devices, augmented reality displays, wearables, and smart devices and healthcare professional input and to transmit that data to the database in both a raw form and a vectorized form for use in training and improving an artificial intelligence system.

11. The system of claim 1, wherein the computer-implemented processor has been configured to use the artificial intelligence including low-rank matrix factorization, vectorization and skip thought vectors to analyze patterns in vectorized patient assessments, genetics, diagnoses, treatments, outcomes, wearables, mobile devices, augmented reality devices, social networks, treatment adherence, and treatment response to suggest current prognosis as well as clinical interventions for an individual patient.

12. The system of claim 1, wherein the computer-implemented processor has been configured to use artificial intelligence including low-rank matrix factorization, vectorization and skip thought vectors to analyze patterns in vectorized patient assessments, genetics, diagnoses, treatments, outcomes, wearables, mobile devices, augmented reality devices, social networks, treatment adherence, and treatment response to suggest continuing or discontinuing treatment as well as discharge prognosis.

13. The system of claim 1, wherein the computer-implemented processor has been configured to use artificial intelligence including low-rank matrix factorization, vectorization and skip thought vectors to analyze patterns in vectorized healthcare professional data including assessment, diagnosis, treatment, intervention, prognosis, homework assignment, theoretical orientation, efficacy rating, discipline, and demographic data to initially suggest prognosis as well as clinical interventions for an individual patient including in-session interventions, patient homework, prescribed activities, and therapeutic orientation.

14. The system of claim 1, wherein the computer-implemented processor has been configured to use artificial intelligence including low-rank matrix factorization, vectorization and skip thought vectors to analyze patterns in vectorized healthcare professional data including assessment, diagnosis, treatment, intervention, prognosis, homework assignment, theoretical orientation, efficacy rating, discipline, and demographic data to suggest current prognosis as well as clinical interventions for an individual patient including in-session interventions, patient homework, prescribed activities, and therapeutic orientation.

15. The system of claim 1, wherein the computer-implemented processor has been configured to use artificial intelligence including low-rank matrix factorization, vectorization and skip thought vectors to analyze patterns in vectorized healthcare professional data including assessment, diagnosis, treatment, intervention, prognosis, homework assignment, theoretical orientation, efficacy rating, discipline, and demographic data to suggest continuing or discontinuing treatment as well as discharge prognosis.

16. A method of providing psychotherapy customized to a patient at a distance, including the steps of:

entering by the patient information about themself into a computing system chosen from the group consisting of symptom data, demographic data, genetic data, diagnostic data, treatment data, history data, outcome data, wearable data, mobile device data, augmented reality device data, social network data, and combinations thereof;

storing the patient information in a database in a vectorized form;

analyzing by the computing system the vectorized patient information via low-rank matrix factorization and suggesting at least one healthcare professional to be used;

selecting by the patient a healthcare professional;

suggesting by the computing system intervention processes to the healthcare professional for the patient based on the patient information, healthcare professional demographic and theoretical orientation data, and vectorized data from previous patients analyzed via low-rank matrix factorization;

creating by the healthcare professional an initial plan of service for the patient based on the suggestions of the system and entering the plan into the system;

connecting the patient to the healthcare professional via real-time image and audio on the computing system to provide in-session therapeutic intervention process based on the initial plan of service;

augmenting the healthcare professional's in-session therapeutic intervention process with real-time data displays about the patient's mood derived from real-time analysis of the patient's speech including tone analysis, and facial expressions including microexpressions, by providing said real-time data to the healthcare professional during the in-session therapeutic intervention process, the healthcare professional providing the service for the patient over the computing system chosen from the group consisting of consultation, education, assessment, diagnosis, intervention, treatment, and combinations thereof;

analyzing by the computing system feedback from the patient in real-time and suggesting by the computing system revisions to the initial plan of service during the in-session therapeutic intervention process, and pushing by the computing system clinical homework activities assigned by the healthcare professional during the in-session therapeutic intervention process to at least one patient device.

\* \* \* \* \*